United States Patent
Gardner et al.

(10) Patent No.: US 11,957,777 B2
(45) Date of Patent: Apr. 16, 2024

(54) COMPOSITIONS COMPRISING REACTION PRODUCTS OF SACCHARIDE POLYMERS AND FATTY ESTERS FORMULATED WITH A NEUTRAL SURFACTANT

(71) Applicant: INTEGRITY BIO-CHEMICALS, LLC, Cresson, TX (US)

(72) Inventors: Christopher P. Gardner, Cresson, TX (US); Stephen William Almond, Creston, CA (US)

(73) Assignee: INTEGRITY BIO-CHEMICALS, LLC, Cresson, TX (US)

( * ) Notice: Subject to any disclaimer, the term of this patent is extended or adjusted under 35 U.S.C. 154(b) by 0 days.

(21) Appl. No.: 18/246,151

(22) PCT Filed: Oct. 26, 2022

(86) PCT No.: PCT/US2022/078692
§ 371 (c)(1),
(2) Date: Mar. 21, 2023

(87) PCT Pub. No.: WO2023/076929
PCT Pub. Date: May 4, 2023

(65) Prior Publication Data
US 2023/0270654 A1 Aug. 31, 2023

Related U.S. Application Data

(60) Provisional application No. 63/272,368, filed on Oct. 27, 2021.

(51) Int. Cl.
*A61K 8/73* (2006.01)
*A61K 8/42* (2006.01)
*A61K 8/92* (2006.01)
*A61Q 19/00* (2006.01)

(52) U.S. Cl.
CPC .................. *A61K 8/73* (2013.01); *A61K 8/42* (2013.01); *A61K 8/922* (2013.01); *A61Q 19/00* (2013.01); *A61K 2800/10* (2013.01); *A61K 2800/5422* (2013.01)

(58) Field of Classification Search
CPC ............................ C08B 30/18; C08B 37/0021
See application file for complete search history.

(56) References Cited

U.S. PATENT DOCUMENTS

| 2004/0235693 A1 | 11/2004 | Wei et al. |
| 2012/0316332 A1 | 12/2012 | Koike et al. |
| 2018/0085299 A1 | 3/2018 | Suzuki et al. |

FOREIGN PATENT DOCUMENTS

| JP | 2017071588 A | 4/2017 |
| KR | 10-2015-0014279 A | 2/2015 |

OTHER PUBLICATIONS

Written Opinion and International Search Report from corresponding PCT Application No. PCT/US2022/078692 dated Feb. 10, 2023.

*Primary Examiner* — Genevieve S Alley
(74) *Attorney, Agent, or Firm* — Vorys, Sater, Seymour and Pease, LLP

(57) ABSTRACT

Compositions comprising a reaction product of a saccharide polymer and a fatty ester may be obtained in an aqueous phase in the presence of a hydroxide base and a neutral surfactant, the saccharide polymer comprising a dextran, a dextrin compound, or any combination thereof. The compositions also comprise one or more alcohols originating from the fatty ester upon forming the reaction product of the saccharide polymer and the fatty ester. The reaction product of the saccharide polymer and the fatty ester may be present in the aqueous phase at a concentration effective to lower a surface tension of the neutral surfactant. The fatty ester may comprise one or more glycerol esters, such as one or more plant and/or animal oils and/or fats, and the one or more alcohols originating from the fatty ester may comprise glycerol. Fatty acids originating from the fatty ester may be substantially straight-chain fatty acids.

21 Claims, No Drawings

COMPOSITIONS COMPRISING REACTION PRODUCTS OF SACCHARIDE POLYMERS AND FATTY ESTERS FORMULATED WITH A NEUTRAL SURFACTANT

BACKGROUND

Amphiphilic compounds having both hydrophobic and hydrophilic regions within their molecular structure are commonly referred to as "surfactants" or "surfactant compounds." By virtue of their molecular structure, surfactants tend to lower the surface tension at an interface between two components. Surfactants may be found in a wide range of consumer and industrial products including, for example, soaps, detergents, cosmetics, pharmaceuticals, and dispersants. In addition, surfactants are also commonly used in the oil and gas industry. Among other functions in these applications and others, surfactants may promote solubility of an otherwise sparingly soluble substance, increase foaming, facilitate emulsification or de-emulsification, and/or lower viscosity in particular instances.

There are difficulties associated with various conventional surfactants. Poor biodegradation, including slow biodegradation in liquid environments, and/or poor biocompatibility of some common synthetic surfactants may impact consumer and industrial products and processes incorporating such surfactants. In addition, some common surfactants may be expensive, have poor aqueous solubility, and/or be subject to environmental and/or other government regulations. Some surfactants may also promote high surface tension values at the critical micelle concentration, which may complicate fluid handling when formulating consumer and industrial products containing such surfactants. A further difficulty associated with conventional surfactants is that the hydrophilic-lipophilic balance (HLB) is fixed by virtue of the molecular structure of the particular amphiphilic compound employed, which may not be suitable for a specified application, even if the surfactant is otherwise chemically compatible with anticipated use conditions.

BRIEF DESCRIPTION OF THE DRAWINGS

Not applicable.

DETAILED DESCRIPTION

The present disclosure generally relates to surfactant technology and, more specifically, compositions comprising a surfactant formed from biologically sourced materials and that may afford low surface tension values in an aqueous phase. The compositions may promote microemulsion formation and/or may themselves be microemulsions in some instances.

As discussed above, conventional surfactants may present various issues such as high cost, lack of biodegradability, poor biocompatibility, and/or poor solubility, which may limit their applicability in various applications. Moreover, there is no easy way to alter the hydrophobic-lipophilic balance (HLB) of conventional surfactants without developing an entirely new chemical synthesis procedure. Surface tension (interfacial tension) values are also frequently high for some types of surfactants as well, which may complicate their handling in various applications and/or preclude formulation thereof into various consumer and industrial products. In addition, some types of surfactants, particularly anionic surfactants, may deleteriously interact with components that may be present in a fluid, such as salts.

The present disclosure provides biopolymer-based compounds that may be produced with tunable addends (substituents) and amounts thereof to tailor surfactant performance (e.g., to adjust HLB) for various applications. Depending on how the biopolymer is functionalized with the addends, the surfactants described herein may promote emulsification or de-emulsification under various circumstances, particularly when combined with a suitable neutral surfactant to provide aqueous phase compositions having low surface tension values. Namely, the present disclosure provides saccharide polymers comprising dextran or dextrin compounds that are reacted with fatty esters under alkaline conditions in an aqueous phase in the presence of the neutral surfactant to afford compositions containing one or more saccharide polymer reaction products and exhibiting unexpectedly low surface tension values. Specifically, when the reaction product of the fatty ester and the saccharide polymer is present in combination with a suitable neutral surfactant or a reaction product form thereof, the surface tension may be lower than that of the neutral surfactant itself. That is, the reaction product of the fatty ester and the saccharide polymer may interact synergistically with the neutral surfactant or a reaction product form thereof to afford decreased surface tension values compared to the neutral surfactant alone at an identical concentration.

As used herein, the term "fatty ester" refers to a compound containing one or more ester moieties, which comprises an alcohol component and a fatty acid component. As used herein, the term "fatty acid" refers to an optionally unsaturated carboxylic acid containing 4 or more carbon atoms. The alcohol component may be a monohydric alcohol or a polyhydric alcohol, such as a diol or triol (e.g., glycerol). The fatty acid may be a straight-chain or branched, saturated or unsaturated fatty acid, examples of which are provided hereinbelow. Preferably, the fatty esters utilized herein contain primarily or exclusively straight-chain optionally unsaturated fatty acids having about 4 to about 30 carbon atoms.

Without being limited by theory, the reaction products described herein may include at least one fatty ester saccharide polymer formed from a reaction between the fatty acid component of the fatty ester and the saccharide polymer (e.g., a dextran or a dextrin compound), which may interact synergistically with the neutral surfactant or a reaction product form thereof to afford low surface tension values. To form the fatty ester saccharide polymer reaction product, the fatty ester may undergo initial hydrolysis under alkaline conditions to generate the fatty acid component or a salt form thereof, which may then react with the saccharide polymer to form the at least one fatty ester saccharide polymer reaction product. Alternately, the fatty ester may undergo direct transesterification with the saccharide polymer to form the at least one fatty ester saccharide polymer reaction product. Any one or more than one of the primary or secondary alcohol functionalities upon the glucose monomer units of the saccharide polymer may undergo a reaction to form a fatty ester saccharide polymer reaction product in the disclosure herein. In the course of forming the fatty ester saccharide polymer reaction product, the alcohol component of the fatty ester may be released into the aqueous phase in which the fatty ester saccharide polymer reaction product is formed. The alcohol component may remain present with the fatty ester saccharide polymer reaction product in the aqueous phase or undergo at least partial removal therefrom. Advantageously and surprisingly, the alcohol component released into the aqueous phase does not significantly impact the low surface tension values attainable when the reaction product and the neutral surfactant are present together. The alcohol component (e.g., glycerol) released into the aqueous phase may aid in solubilizing other components of the composition and/or other components blended with the compositions to make various consumer and industrial products. Optionally, additional alcohol (beyond that released from the fatty ester when forming the reaction product), including monohydric alcohols and/or polyhydric alcohols other than glycerol, may be added to the compositions in response to particular formulation needs.

Components used for forming the reaction products of the present disclosure individually tend to raise surface tension values. Surprisingly, once all combined together and a reaction product has been formed from at least a portion of the individual components, the surface tension of cocamide diethanolamine (CocoDEA) and similar alkanolamide neutral surfactants may be unexpectedly lowered, possibly after a further reaction of an alcohol functionality of the alkanolamide neutral surfactant occurs. Similar neutral surfactants that may function in a like manner to CocoDEA and undergo lowering of the surface tension include, but are not limited to, other fatty acid alkanolamides, such as cocamide diisopropanolamine (CocoDIPA) or those formed from palmitic acid or other fatty acids and ethanolamine, diethanolamine, or diisopropanolamine, for example.

Further, reaction products of the present disclosure having a sufficiently high HLB value may promote foaming of formulations, including when combined with one or more suitable surfactants. The combination of a neutral surfactant and reaction products of the present disclosure may promote ready foaming of an aqueous fluid, and may afford a more stable foam than does a comparable mass of ionic surfactant, including cationic, anionic, or zwitterionic surfactants. A zwitterionic surfactant may optionally be combined with the reaction products of the present disclosure to improve foaming performance relative to that attainable with the reaction products and a neutral surfactant alone. Given the biomolecule nature of the reaction products, foamed or foamable formulations comprising one or more reaction products of the present disclosure may represent a more environmentally friendly approach for formulating soaps and other personal care products intended to undergo foaming. Other surprising results may be realized when combining a suitable zwitterionic surfactant with the reaction products of the present disclosure in some cases.

In addition to affording foamed or foamable formulations based at least in part upon neutral surfactant technology, the reaction products of the present disclosure may fully or partially replace more costly surfactants and/or surfactants subject to government regulations in various industrial or consumer products. For example, the reaction products of the present disclosure may be an effective full or partial replacement for ethoxylated alcohol neutral surfactants. The lowering of surface tension afforded by the reaction products of the present disclosure in combination with a neutral surfactant may also be advantageous when replacing a less desirable surfactant, particularly if the less desirable surfactant tends to increase surface tension values or is overly expensive.

Thus, the reaction products of the present disclosure may be advantageous due to their biological origin, low cost and ability to afford low surface tension values when present in combination with a suitable neutral surfactant. Reaction products of maltodextrin, for example, represent a particularly useful class of dextrin-based reaction products due to the low cost and convenient molecular weight range of this saccharide polymer. A number of fats, oils and similar glycerol esters may serve as convenient and inexpensive sources for the fatty ester used in forming the reaction products described herein. Moreover, fats, oils and similar glycerol esters and amounts thereof may be selected to promote tailoring of the surfactant properties, such as altering HLB values and/or determining whether emulsifying or de-emulsifying performance results in a particular circumstance, for instance. Naturally occurring fats and oils may be a particularly convenient source of straight-chain fatty acids for use in the reaction products disclosed herein.

Maltodextrins may represent an advantageous saccharide polymer for use in the disclosure herein due to their low cost, environmentally benign nature, and the relative ease with which they may be chemically reacted with various fatty acids originating from a fatty ester, such as a glycerol ester. Depending on the fatty acid(s) reacted with a maltodextrin, the hydrophobic-lipophilic balance (HLB) of the reaction products may range from about 5 to about or more, wherein known molecular contributions may be utilized to calculate the HLB value. Thus, maltodextrin reaction products may be effective for forming emulsions in substantially water-based fluids or substantially oil-based fluids, with particular fatty acid(s) and a fatty ester source and amount thereof being selected for a reaction with the maltodextrin based upon specified conditions anticipated to be present in a given application. The ability to readily adjust the HLB of the reaction products represents a significant advantage when formulating consumer and industrial products according to the disclosure herein.

In addition to property variation resulting from the fatty acid size, maltodextrins are available in a range of oligomer sizes (e.g., 3-20 glucose monomers, or even up to about 25 glucose monomers), which may allow further property tailoring to be realized. As such, maltodextrin reaction products may offer numerous advantages and a wide range of applicability in various applications and formulations in which surfactants are commonly used, such as in soaps and other personal care products. Dextran reaction products may offer similar advantages and features to those of maltodextrin reaction products, including the ability to produce low surface tension values.

Maltodextrin and other dextrin compounds suitable for use in the present disclosure may comprise 2 to about 20 glucose monomers, or even up to about 25 glucose monomers, linked together with $\alpha(1,4)$ glycosidic bonds. At least a portion of the glucose monomers may form a reaction product upon being contacted under suitable conditions with a fatty ester and/or a fatty acid salt originating from a fatty ester, such as a salt of a $C_4$-$C_{30}$ fatty acid or a $C_4$-$C_{20}$ fatty acid. Without being limited by theory, at least a portion of the glucose monomers in the dextrin compound may react to form a fatty ester dextrin compound, which may be optionally present in combination with unreacted fatty acid salt in the aqueous phase defining the compositions disclosed herein. When formed, a fatty ester reaction product may form at any hydroxyl group of the dextrin compound, including any combination of primary and/or secondary hydroxyl groups. Hydroxyl groups upon the neutral surfactant may undergo a similar esterification reaction under the same reaction conditions.

Dextran is a saccharide polymer characterized by predominantly $\alpha(1,6)$ glycosidic bonds between adjacent glucose monomers, with a limited number of glucose side chains linked to the main polymer backbone via $\alpha(1,3)$ glycosidic bonds. The $\alpha(1,3)$ glycosidic bonds may introduce crosslinks between adjacent saccharide polymer chains. Depending on the biological source, the extent of branching and the molecular weight of dextran may vary considerably, any of which may be utilized in the disclosure herein. At least a portion of the glucose monomers in dextran may form a reaction product upon being contacted under suitable conditions with a fatty ester or a fatty acid salt originating from a fatty ester, such as a salt of a $C_4$-$C_{30}$ fatty acid or a $C_4$-$C_{20}$ fatty acid. Without being limited by theory, at least a portion of the glucose monomers may react to form a fatty ester dextran in some embodiments, which may be optionally present in combination with unreacted fatty acid salt in the aqueous phase defining the compositions disclosed herein. When formed, a fatty ester reaction product may form at any hydroxyl group of the dextran.

In some embodiments, reaction products of the present disclosure may include a dextrin compound having 3 to about 20 glucose monomers, or even up to about 25 glucose monomers, that are covalently linked by α(1,4) glycosidic bonds. Formula 1 below shows the generic structure of a dextrin compound having only α(1,4) glycosidic bonds between adjacent glucose monomers, wherein variable 'a' is a positive integer ranging from 1 to about 18, thereby providing a dextrin backbone with 3 to about 20 glucose monomers. In the case of a dextrin compound containing up to 25 glucose monomers, variable 'a' may range from 1 up to about 23. The terminal glucose unit is shown in its closed form, but may also be present in the corresponding reducing sugar (open chain or acyclic) form as well.

Other dextrin compounds may contain only α(1,6) glycosidic bonds or a mixture of α(1,4) and α(1,6) glycosidic bonds, and such dextrin compounds may also be suitable for use in forming the reaction products of the present disclosure. Particularly suitable dextrins may have a molecular weight (e.g., $M_n$) in the range of about 1200 to about 1400 or about 1100 to about 1500.

In some or other embodiments, the reaction products may include a dextran obtained from any suitable source. The structure of dextran is shown in Formula 2 below, in which the α(1,3) glycosidic bonds are not shown in the interest of clarity. Where they occur, the α(1,3) glycosidic bonds may append a terminal glucose monomer as a side chain to the α(1,6)-linked saccharide polymer backbone, form crosslinks between adjacent α(1,6)-linked saccharide polymer backbones, interrupt the α(1,6)-linked saccharide polymer backbone with an α(1,3) glycosidic bond, or any combination thereof. Depending on source, up to about 5% of the glucose Formula 1

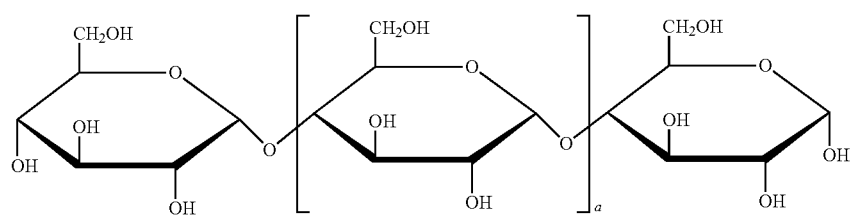

monomers may be linked by α(1,3) glycosidic bonds. Linkage by α(1,3) glycosidic bonds may occur upon any of the glucose monomers. The numbering of a single glucose monomer is shown in Formula 3 below.

Formula 2

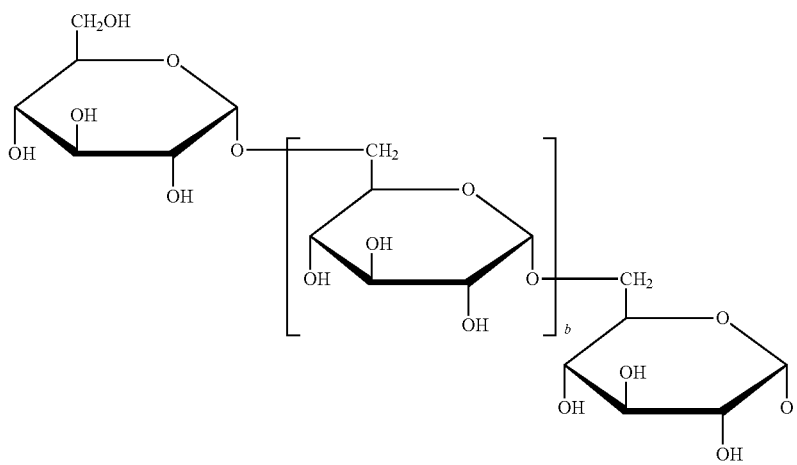

Suitable dextrans may have a molecular weight of about 1200, or about 1400, or about 5000 up to about 50,000,000, or about 100,000 up to about 20,000,000. As such, variable 'b' may range from about 30 to about 300,000 depending on the particular dextran selected. Particularly suitable dextrans may have a molecular weight (e.g., $M_n$) ranging from about 1200 to about 1400, or about 1100 to about 1500, or about 1000 to about 100,000, or about 100,000 to about 1 million, or about 2 million to about 5 million, or about 5 million to about 50 million. Another suitable dextran may have a molecular weight of about 500,000 and an activity level of about 9%.

Formula 3

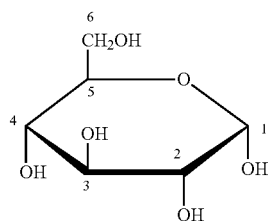

The saccharide polymer may comprise a maltodextrin according to some embodiments of the present disclosure. Maltodextrins may be characterized in terms of their dextrose equivalent (DE) value. Dextrose equivalent is a measure of the amount of reducing sugars (e.g., glucose monomers) that are present in a saccharide polymer, particularly a dextrin, expressed as a percentage relative to dextrose. Starch, which is functionally non-reducing, has a defined dextrose equivalent of 0, whereas dextrose itself has a dextrose equivalent of 100. Dextrose equivalent may be calculated by dividing the molecular weight of glucose by $M_n$ and multiplying the result by 100. Higher dextrose equivalent values are characteristic of a lower number of covalently linked glucose monomers (shorter polymer backbone length, thereby providing a higher relative percentage of terminal reducing sugars). Maltodextrins suitable for forming a reaction product with one or more fatty esters according to the disclosure herein may exhibit dextrose equivalent values ranging from 3 to about 25 or from 3 to about 20. In more specific embodiments, dextrose equivalent values of the maltodextrins may range from about 4.5 to about 7.0, or from about 7.0 to about 10.0, or from about 9.0 to about 12.0.

Maltodextrins suitable for forming a reaction product may be obtained from hydrolysis or pyrolysis of starch, specifically the amylose component of starch, according to some embodiments. A maltodextrin having Formula 1 may be formed by hydrolysis or pyrolysis of amylose, for example. Alternative suitable dextrins may be obtained from hydrolysis or pyrolysis of the amylopectin component of starch, in which case the dextrin may contain $\alpha(1,6)$ glycosidic bonds if the dextrin is obtained through hydrolysis of the amylopectin side chain. Starches from which the dextrins may be subsequently produced may be obtained from any starch source.

Accordingly, reaction products of the present disclosure may comprise an aqueous phase, a neutral surfactant or a reaction product form thereof, a reaction product of a saccharide polymer and a fatty ester, in which the saccharide polymer comprises a dextran, a dextrin compound, or any combination thereof, and the reaction product of the saccharide polymer and the fatty ester and the reaction product form of the neutral surfactant, if present, are formed in the aqueous phase in the presence of a hydroxide base (e.g., under alkaline conditions). The fatty ester has at least one alcohol component and at least one fatty acid component that may be liberated under the alkaline conditions. Suitable hydroxide bases may include, for example, alkali metal hydroxides, such as sodium hydroxide, potassium hydroxide, or any combination thereof. A stoichiometric excess or a stoichiometric deficit of the hydroxide base relative to an amount of the fatty ester may be present. The compositions may further comprise one or more alcohols originating from the fatty ester upon forming the reaction product of the saccharide polymer and the fatty ester. The reaction product of the saccharide polymer and the fatty ester may be present in the aqueous phase at a concentration effective to lower a surface tension of the neutral surfactant.

A molar ratio of fatty acid (originating from the fatty ester) to glucose monomers in the reaction product may be about 0.05 or above on a basis of $\text{moles}_{fatty\ acid\ in\ fatty\ ester}:\text{moles}_{glucose\ monomers\ in\ saccharide\ polymer}$, or about 0.08 or above on a basis of $\text{moles}_{fatty\ acid\ in\ fatty\ ester}:\text{moles}_{glucose\ monomers\ in\ saccharide\ polymer}$, or about 0.1 or above on a basis of $\text{moles}_{fatty\ acid\ in\ fatty\ ester}:\text{moles}_{glucose\ monomers\ in\ saccharide\ polymer}$, or about 0.2 or above on a basis of $\text{moles}_{fatty\ acid\ in\ fatty\ ester}:\text{moles}_{glucose\ monomers\ in\ saccharide\ polymer}$, or about 0.3 or above on a basis of $\text{moles}_{fatty\ acid\ in\ fatty\ ester}:\text{moles}_{glucose\ monomers\ in\ saccharide\ polymer}$, or about 0.4 or above on a basis of $\text{moles}_{fatty\ acid\ in\ fatty\ ester}:\text{moles}_{glucose\ monomers\ in\ saccharide\ polymer}$, or about 0.5 or above on a basis of $\text{moles}_{fatty\ acid\ in\ fatty\ ester}:\text{moles}_{glucose\ monomers\ in\ saccharide\ polymer}$, or about 0.6 or above on a basis of $\text{moles}_{fatty\ acid\ in\ fatty\ ester}:\text{moles}_{glucose\ monomers\ in\ saccharide\ polymer}$, or about 0.7 or above on a basis of $\text{moles}_{fatty\ acid\ in\ fatty\ ester}:\text{moles}_{glucose\ monomers\ in\ saccharide\ polymer}$, or about 0.8 or above on a basis of $\text{moles}_{fatty\ acid\ in\ fatty\ ester}:\text{moles}_{glucose\ monomers\ in\ saccharide\ polymer}$, or about 0.9 or above on a basis of $\text{moles}_{fatty\ acid\ in\ fatty\ ester}:\text{moles}_{glucose\ monomers\ in\ saccharide\ polymer}$. A maximum ratio of fatty acid to dextrin or dextran in the reaction product, based upon glucose monomers, may be about 1.0 in most cases, although molar ratios above 1.0 also reside within the scope of the present disclosure. The foregoing ratios may represent a molar ratio of fatty acid reacted with the dextran or dextrin compound. Thus, in some embodiments, the molar ratio of fatty acid to glucose monomers in the reaction product may range from about 0.05 $\text{moles}_{fatty\ acid\ in\ fatty\ ester}:\text{moles}_{glucose\ monomers\ in\ saccharide\ polymer}$ to about 1.0 $\text{moles}_{fatty\ acid\ in\ fatty\ ester}:\text{moles}_{glucose\ monomers\ in\ saccharide\ polymer}$, or about 0.05 $\text{moles}_{fatty\ acid\ in\ fatty\ ester}:\text{moles}_{glucose\ monomers\ in\ saccharide\ polymer}$ to about 0.9 $\text{moles}_{fatty\ acid\ in\ fatty\ ester}:\text{moles}_{glucose\ monomers\ in\ saccharide\ polymer}$, or about 0.05 $\text{moles}_{fatty\ acid\ in\ fatty\ ester}:\text{moles}_{glucose\ monomers\ in\ saccharide\ polymer}$ to about 0.8 $\text{moles}_{fatty\ acid\ in\ fatty\ ester}:\text{moles}_{glucose\ monomers\ in\ saccharide\ polymer}$, or about 0.05 $\text{moles}_{fatty\ acid\ in\ fatty\ ester}:\text{moles}_{glucose\ monomers\ in\ saccharide\ polymer}$ to about 0.7 $\text{moles}_{fatty\ acid\ in\ fatty\ ester}:\text{moles}_{glucose\ monomers\ in\ saccharide\ polymer}$, or about 0.05 $\text{moles}_{fatty\ acid\ in\ fatty\ ester}:\text{moles}_{glucose\ monomers\ in\ saccharide\ polymer}$ to about 0.6 $\text{moles}_{fatty\ acid\ in\ fatty\ ester}:$ The ratio $$\frac{\text{moles}_{\textit{fatty acid in fatty ester}}}{\text{moles}_{\textit{glucose monomers in saccharide polymer}}}$$

may range from or about 0.05 to about 0.5; or about 0.05 to about 0.4; or about 0.1 to about 0.9; or about 0.1 to about 0.8; or about 0.1 to about 0.7; or about 0.1 to about 0.6; or about 0.1 to about 0.5; or about 0.1 to about 0.4; or about 0.2 to about 0.9; or about 0.2 to about 0.8; or about 0.2 to about 0.7; or about 0.2 to about 0.6; or about 0.2 to about 0.5; or about 0.2 to about 0.4; or about 0.3 to about 0.9; or about 0.3 to about 0.8; or about 0.3 to about 0.7; or about 0.3 to about 0.6; or about 0.3 to about 0.5; or about 0.3 to about 0.4; or about 0.4 to about 0.9; or about 0.4 to about 0.8; or about 0.4 to about 0.7; or about 0.4 to about 0.6; or about 0.4 to about 0.5. One or more hydroxyl groups per glucose monomer may undergo a reaction in some cases, particularly at a molar ratio of about 1.0 or above. At least a portion of the glucose monomers may remain unfunctionalized, particularly at lower molar ratios. Unreacted fatty acids, if any, may remain in the reaction product as a fatty acid salt of the hydroxide base.

As such, reaction products of the present disclosure may comprise one or more fatty ester dextrins and/or one or more fatty ester dextrans, optionally in further combination with a fatty acid salt (e.g., an alkali metal carboxylate), and/or a hydroxide base (e.g., an alkali metal hydroxide base). The hydroxide base may be present in at least a sufficient molar quantity to react with at least a portion of the fatty ester to promote hydrolysis thereof and to convert the fatty acid component of the fatty ester into a fatty acid salt (e.g., an alkali metal carboxylate). The alcohol component released from the fatty ester following hydrolysis may be present in combination with any of the reaction products as well. The hydroxide base may be neutralized with an acid or removed through washing, and compositions comprising the reaction products may retain a low surface tension following neutralization or washing. The alcohol component may be removed from the compositions as well, if desired, such as through distillation or solvent extraction, for example.

Alternately, other saccharide polymers may be utilized to form the reaction products in the compositions described herein. Other saccharide polymer that may be used in this regard include, but are not limited to, glycogen, guar, xanthan, welan, scleroglucan, chitosan, schizophyllan, levan, pectins, inulin, arabinoxylans, pullulan, gellan, carrageenan, chitosan, chitin, cellulose, starch, or a combination thereof. Saccharide polymer fragments obtained from the foregoing and containing about 3 to about 25 monomers per fragment may also be utilized for forming the reaction products described herein.

Compositions of the present disclosure may comprise a neutral surfactant in combination with the foregoing reaction products, optionally in further combination with a zwitterionic surfactant. Surprisingly, the reaction products of the present disclosure may promote lowering of the surface tension of the neutral surfactant. That is, the reaction products may be present in an effective concentration to lower the surface tension of the neutral surfactant compared to that of the neutral surfactant alone at a substantially similar concentration in the aqueous phase. Neutral surfactants may be useful due to their already-low surface tension values. When combined with the saccharide polymer during formation of the reaction product according to the disclosure herein, alcohol groups upon a neutral surfactant, such as those present upon an alkanolamide neutral surfactant, may form a reaction product as well, such as with a fatty acid component liberated from a fatty ester, for example.

Suitable neutral surfactants that may have their surface tension lowered in combination with a reaction product of the present disclosure include cocamide-based surfactants such as cocamide diethanolamine, cocamide monoethanolamine, cocamide monoisopropanolamine, cocamide diisopropanolamine, and the like. Cocamide diethanolamine (CocoDEA) or cocamide diisopropanolamine (CocoDIPA) may be particularly suitable neutral surfactants for use in the disclosure herein. Other neutral surfactants that may be suitable include additional fatty acid amide alkanolamines (alkanolamides), such as palmitic acid diethanolamide, monoethanolamide, or diisopropanolamide. In the compositions of the present disclosure, such neutral surfactants may be present at a concentration of about 20 wt. % or less, or about 10 wt. % or less, or about 5 wt. % or less, such as about 1 wt. % to about 10 wt. %, or about 3 wt. % to about 8 wt. %, each based on total mass of the composition.

Zwitterionic surfactants, such as cocamidopropyl betaine, may also be present in the compositions of the present disclosure in some instances, either alone or in combination with a neutral surfactant, particularly when producing foamable formulations comprising the reaction products. Zwitterionic surfactants may likewise have their surface tension lowered when combined with the reaction products. Another type of suitable zwitterionic surfactant that may be present in combination with an alkanolamide neutral surfactant include various sultaines, such as cocoamidopropyl hydroxysultaine. Additional surprising benefits may be realized when an alkanolamide neutral surfactant and a zwitterionic surfactant are present in combination with one another in some cases.

Once formed, the pH of compositions containing the reaction products disclosed herein may reside within a range of about 1 to about 14, such as a range of about 1 to about 5, or about 5 to about 7, or about 7 to about 9, or about 9 to about 14. The pH may be raised or lowered, if needed, after forming the reaction products in accordance with the disclosure herein. Lower surface tension values may be realized as the pH decreases in some instances. Decreased surface tension may also be realized in the presence of dissolved salt, such as potassium chloride.

Reaction products of the present disclosure, which may include those formed through a reaction of one or more fatty esters with a dextrin compound and/or a dextran, may be prepared by a process comprising: heating a saccharide polymer comprising a dextran, a dextrin compound (e.g., comprising 3 to about 20 glucose monomers, or even up to about 25 glucose monomers, linked together with $\alpha(1,4)$ glycosidic bonds, such as maltodextrin), or any combination thereof, a fatty ester, a neutral surfactant and a hydroxide base in an aqueous phase, and obtaining a reaction product of the saccharide polymer and the fatty ester in the aqueous phase. The aqueous phase may further contain one or more alcohols originating from the fatty ester and the neutral surfactant or a reaction product form thereof. The reaction product may be present in the aqueous phase at a concentration effective to lower a surface tension of the neutral surfactant, as measured relative to the neutral surfactant alone at a like concentration in the aqueous phase. For example, a 5 wt. % solution of the neutral surfactant in water may have a higher surface tension than does a composition containing 5 wt. % of the neutral surfactant in combination with a reaction product of the present disclosure in a surface tension-lowering amount. A zwitterionic surfactant may be combined with the reaction product in some cases. Any of the reaction products of a dextran or a dextrin compound may constitute a suitable saccharide polymer for forming compositions having a low surface tension. Heating may be conducted at a temperature of about 100° C. or less, such as at about 50° C. to about 80° C., or about 60° C. to about 70° C., or about 50° C. to about 60° C.

In the presence of a neutral surfactant, surface tension values for the compositions of the present disclosure may be about 40 dynes/cm or less, or about 38 dynes/cm or less, or about 36 dynes/cm or less, or about 34 dynes/cm or less, or about 32 dynes/cm or less, or about 30 dynes/cm or less, or about 28 dynes/cm or less. Alternately, the surface tension values may be lowered up to about 40% relative to the surface tension of the neutral surfactant in the aqueous phase alone at a like concentration, or lowered up to about 30%, or lowered up to about 20%, or lowered up to about 15%, or lowered up to about 10%. In a particular example, the surface tension may be lowered in an amount of about 10% to about 25%, or about 10% to about 20%, or about 15% to about 25%, as measured relative to the surface tension of the neutral surfactant in the aqueous phase alone at a substantially identical concentration to that in a composition containing the reaction product. The surface tension and lowering thereof may be largely governed by the amount of neutral surfactant that is present (higher concentrations of neutral surfactant may afford lower surface tension values), with the chosen amount of neutral surfactant being selected to provide a desired extent of surfactancy for a given application. At the chosen amount of neutral surfactant, the reaction product may be present in an amount sufficient to lower the surface tension relative to the surface tension that would otherwise be obtained for the neutral surfactant alone at a substantially identical concentration in an aqueous phase.

In forming the reaction products of the present disclosure, methods of the present disclosure may comprise combining the fatty ester, the hydroxide base, and the neutral surfactant in water to form a mixture, and heating the mixture until the fatty ester dissolves (e.g., by undergoing hydrolysis) and a homogeneous mixture forms. The saccharide polymer may be combined with the fatty ester during this process, or the saccharide polymer may be combined with the homogeneous mixture after formation thereof. Once the saccharide polymer is present in the homogeneous mixture, heating may be continued until the reaction product has formed to a sufficient degree. The resulting aqueous phase may be utilized directly in further applications, optionally after concentration, neutralization, or dilution, or by being further combined with additional components targeted for a particular formulation. Formulations and products in which compositions of the present disclosure may be utilized are discussed hereinbelow. In some instances, the compositions may at least partially replace another surfactant in a specific formulation, such as a charged surfactant. In other instances, the compositions may at least partially replace an ethoxylated alcohol surfactant in a formulation.

Suitable fatty esters for forming reaction products are not believed to be particularly limited, provided that the fatty esters undergo effective hydrolysis to release an alcohol component and one or more fatty acid components of the fatty ester into the aqueous phase. Fatty acids originating from the fatty esters and suitable for forming reaction products of the present disclosure may be selected (through selection of a suitable fatty ester containing one or more desired fatty acids) to afford reaction products having a range of HLB values, such as HLB values of about 5 to about 20. Illustrative fatty esters are provided below. The fatty acids originating from the fatty esters may range in size from about $C_4$ to about $C_{30}$, or about $C_4$ to about $C_{20}$, or about $C_6$ to about $C_{18}$, or about $C_8$ to about $C_{24}$. Suitable fatty acids for forming a reaction product according to the disclosure herein may be straight chain or branched, and saturated or unsaturated. Illustrative fatty acids that may be suitable for forming a reaction product of the present disclosure include, for example, butyric acid, valeric acid, caproic acid, enanthic acid, caprylic acid, pelabonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, trioscylic acid, lignoceric acid, pentacosylic acid, cerotic acid, carboceric acid, montanic acid, nonacosylic acid, melissic acid, crotonic acid, cervonic acid, linoleic acid, linolelaidic acid, linolenic acid, arachidonic acid, docosatetraenoic acid, myristoleic acid, palmitoleic acid, sappenic acid, vaccenic acid, paullinic acid, oleic acid, pinolenic acid, stearidonic acid, eleostearic acid, elaidic acid, gondoic acid, gadoleic acid, erucic acid, eicosenoic acid, eicosadiencoic acid, eicosatrienoic acid, eicosatetraenoic acid, docosadienoic acid, nervonic acid, mead acid, adrenic acid, the like, and any combination thereof.

Preferably, the fatty acid(s) obtained from a fatty ester comprise at least about 60 wt. % of one or more straight-chain fatty acids, or at least about 70 wt. % of one or more straight-chain fatty acids, or at least about 80 wt. % of one or more straight-chain fatty acids, or at least about 90 wt. % of one or more straight-chain fatty acids, or at least about 95 wt. % of one or more straight-chain fatty acids, or at least about 98 wt. % of one or more straight-chain fatty acids, or at least about 99 wt. % of one or more straight-chain fatty acids. Fatty acids released from naturally occurring fats and oils may substantially comprise straight-chain fatty acids. Accordingly, the at least one fatty acid from the fatty ester in the reaction products disclosed herein may comprise about 90 wt. % or above straight-chain fatty acids, or about 95 wt. % or above straight-chain fatty acids, or about 98 wt. % or above straight-chain fatty acids, or the at least one fatty acid in the reaction products may consist of or consist essentially of straight-chain fatty acids. Preferably, at least one unsaturated fatty acid, such as oleic, linoleic or linolenic acid, may be present in the reaction product, since the fatty ester may be sourced from naturally occurring plant or animal oils, as discussed further below, in which these unsaturated fatty acids commonly occur.

In some embodiments, the fatty ester may comprise a glycerol ester of at least one fatty acid. A glycerol ester may undergo alkaline hydrolysis to liberate glycerol as an alcohol component, and up to three fatty acid components per glycerol alcohol component may be released when undergoing a reaction with a saccharide polymer according to the disclosure herein. The fatty acid components released from the glycerol ester may be the same or different, and at least one unsaturated fatty acid may be among the fatty acid components, according to some embodiments of the present disclosure. When one or more fatty acids are obtained from a glycerol ester that is a naturally occurring plant or animal oil, at least about 90 wt. %, or at least about 95 wt. %, or at least about 98 wt. % of the fatty acids within the glycerol ester, based on total fatty acids, may comprise one or more straight-chain fatty acids. Preferably, a fatty ester that is a plant or animal oil may consist of or consist essentially of one or more optionally unsaturated straight-chain fatty acids.

Glycerol esters suitable for forming a reaction product in accordance with the disclosure herein are not believed to be particularly limited and may comprise any plant oil, animal oil, plant fat, animal fat, or any combination thereof that contains or more desired fatty acids. The glycerol ester may undergo hydrolysis or transesterification in the course of forming a reaction product with a saccharide polymer. Suitable glycerol esters may be found in plant or animal sources including, for example, soybean oil, grapeseed oil, olive oil, palm oil, rice bran oil, safflower oil, corn oil, coconut oil, sunflower seed oil, canola oil, rapeseed oil, peanut oil, cottonseed oil, hazelnut oil, tea seed oil, linseed oil, sesame oil, acai oil, almond oil, beech nut oil, brazil nut oil, cashew oil, macadamia nut oil, pecan oil, pine nut oil, pistachio oil, walnut oil, pumpkin seed oil, apricot oil, avocado oil, grapefruit oil, lemon oil, orange oil, mango oil, flax seed oil, fish oil, cocoa butter, hemp oil, castor oil, tall oil, fish oil, cattle fat, buffalo fat, sheep fat, goat fat, duck fat, pig fat, poultry fat, and any combination thereof.

Soybean oil, for example, contains a mixture of saturated and unsaturated straight-chain fatty acids, predominantly palmitic acid, stearic acid, oleic acid, linoleic acid, and linolenic acid, with the monounsaturated and polyunsaturated fatty acids (oleic acid, linoleic and linolenic acids) comprising a majority of the fatty acids obtainable from the soybean oil. Palm oil contains about 50% saturated straight-chain fatty acids (palmitic acid, stearic acid, and myristic acid) and 50% unsaturated straight-chain fatty acids (oleic acid, linoleic acid, and linolenic acid). Coconut oil contains predominantly saturated straight-chain fatty acids (caprylic acid, capric acid, lauric acid, myristic acid, palmitic acid, and stearic acid) and less than 10% unsaturated straight-chain fatty acids (oleic acid and linoleic acid). Saturated fats, which are also fatty acids, may contain substantially saturated straight-chain fatty acids.

When glycerol esters are used as a direct (in situ) source of fatty acids for formation of reaction products of the present disclosure, glycerol may be present as the at least one alcohol in compositions containing the reaction products. Optionally, the glycerol may be at least partially removed from the aqueous phase of the compositions, if desired. Otherwise, the amount of glycerol present in the compositions may be dictated by the amount of glycerol ester that is present when forming the reaction product. For example, for glycerol esters containing $C_8$-$C_{24}$ fatty acids, the weight percentage of glycerol in the glycerol esters may range from about 7 wt. % to about 17 wt. %, based on total mass of the glycerol ester. Accordingly, the corresponding weight percentages of glycerol in compositions containing the reaction product, as measured relative to the fatty acid(s) originating from the glycerol ester upon alkaline hydrolysis, may range from about 7.5 wt. % to about 20 wt. %. Alternately, the weight percentage of glycerol in the compositions may be substantially equivalent on a mass basis, with respect to the entirety of the composition, to the weight percentage of glycerol ester present in the reaction mixture, since each glycerol ester may release one glycerol molecule upon undergoing complete hydrolysis.

Methods of the present disclosure may further comprise inducing foam formation in the aqueous phase after obtaining the reaction product therein, optionally after further combining the reaction product with water and/or adding additional components. As used herein, the term "foam" refers to a stabilized dispersion of a large volume of gas in the form of bubbles of varying sizes in a relatively small volume of liquid. Inducing foam formation of the aqueous phase may take place by agitating the aqueous phase in the presence of a gas, such as through stirring or blending in the presence of the gas, bubbling gas through the aqueous phase, or any combination thereof.

Gases suitable for forming a foam in the presence of the reaction products are not believed to be particularly limited. Suitable gases for forming a foam may include, but are not limited to, air, nitrogen, carbon dioxide, helium, natural gas, or any combination thereof. Aerosol propellants may also be used in some instances.

As used herein, the term "foam quality" refers to the percentage of gas in a volume of foam and may be calculated by dividing the quantity (total foam volume-liquid volume) by the total foam volume. Foams formed according to the disclosure herein may have a foam quality of about 10% or above, or about 20% or above, or about 30% or above, or about 40% or above, or about 50% or above, or about 60% or above, or about 70% or above, or about 80% or above, or about 90% or above. The upper limit of the foam quality may be about 99%, or about 95%, or about 90%, or about 80%, or about 70%, or about 60% or about 50%.

Foamed or foamable formulations of the present disclosure may comprise an aqueous phase comprising an aqueous carrier fluid, which is described in more detail hereinafter. Foamed formulations (foams) are compositions to which a gas has already been introduced and foam bubbles have formed. That is, foamed formulations may comprise a gas, and an aqueous fluid comprising a composition described herein admixed together with the gas as a plurality of bubbles. Foamable formulations, in contrast, are compositions suitable for forming a foam once a gas has been introduced thereto, but which have not yet formed foam bubbles.

In addition to the reaction products of the present disclosure, foamed or foamable formulations may further comprise one or more additional surfactants beyond the neutral surfactant promoting a low surface tension. The one or more additional surfactants may be cationic, anionic, zwitterionic, neutral, or any combination thereof. Foamed or foamable formulations may also contain additional components found in soaps and other personal care products, examples of which will be familiar to persons having ordinary skill in the art. Additional disclosure directed to industrial and consumer products, including personal care products and foamed variants thereof, in which the compositions described herein may be present are discussed in further detail below.

Reaction products may be provided, sourced, mixed, or stored in solid form or in liquid form. Liquid forms may be disposed in a suitable fluid phase, such as an aqueous phase, which may be emulsified (including microemulsion forms) or non-emulsified depending on particular formulations and intended applications. In addition, the aqueous phase may be foamed in some instances. As used herein, the terms "fluid" and "fluid phase" refer to both liquids and gels, including solutions, emulsions and suspensions of the reaction products, including foams, unless otherwise indicated. Compositions including a reaction product of the present disclosure may comprise an aqueous carrier fluid. Suitable aqueous carrier fluids may include, for example, fresh water, acidified water, seawater, brine (i.e., a saturated salt solution), or an aqueous salt solution (i.e., a non-saturated salt solution). Water-miscible organic co-solvents such as ethanol or ethylene glycol, for example, may be present in combination with an aqueous carrier fluid, in some embodiments, any of which may be optionally present in combination with glycerol. Suitable aqueous carrier fluids may be present while forming the reaction products, or an aqueous carrier fluid may be introduced to the reaction products following their formation.

Subterranean Treatment Operations

The recovery of hydrocarbon resources, such as oil and gas, from subterranean formations is often performed in conjunction with introducing one or more subterranean treatment chemicals downhole. As used herein, the terms "treat," "treatment," "treating," and grammatical equivalents thereof refer to any compound, fluid, or combination thereof that is introduced to a subterranean formation with the goal of achieving a desired function and/or for a desired purpose. A suitable treatment chemical may be selected based upon particular conditions present or anticipated to be present downhole.

Reaction products of the present disclosure, including those formed from maltodextrin, other dextrin compounds, or dextran may be formulated as a subterranean treatment fluid. Treatment fluids may be used in a variety of subterranean treatment operations to facilitate or promote a desired outcome within the subterranean formation. As used herein, the term "treatment fluid" refers to any fluid used in a subterranean treatment operation in conjunction with achieving a desired function and/or for a desired purpose. Unless otherwise specified, use of the term "treatment fluid" does not imply any particular action by the treatment fluid or a component thereof. Illustrative treatment operations that may be facilitated through use of the reaction products of the present disclosure include, without limitation, drilling operations, stimulation operations, production operations, remediation operations, sand control operations, and the like, which may include, for example, fracturing operations, gravel packing operations, acidizing operations, descaling operations, consolidation operations, workover operations, cleanup operations, diversion operations, and the like. Any of these treatment operations may feature emulsification, de-emulsification, a change in surface wetting characteristics downhole, or any combination thereof.

As used herein, the term "drilling operation" refers to the process of forming a wellbore in a subterranean formation. As used herein, the term "drilling fluid" refers to a fluid used in drilling a wellbore.

As used herein, the term "stimulation operation" refers to an activity conducted within a wellbore to increase production therefrom. As used herein, the term "stimulation fluid" refers to a fluid used downhole during a stimulation activity to increase production of a hydrocarbon resource from the subterranean formation. In some instances, stimulation fluids may include a fracturing fluid or an acidizing fluid.

As used herein, the terms "clean-up operation" or "damage control operation" refer to any operation for removing extraneous material from a wellbore to increase production. As used herein, the terms "clean-up fluid" or "damage control fluid" refer to a fluid used for removing an unwanted material from a wellbore that otherwise blocks flow of a desired fluid therethrough. In one example, a clean-up fluid can be an acidified fluid for removing material formed by one or more perforation treatments. In another example, a clean-up fluid can be used to remove a filter cake upon the wellbore walls. For example, a reaction product of the present disclosure may promote liberation of a hydrocarbon resource from a subterranean formation to promote wellbore cleanup by changing surface wetting characteristics. In another embodiment, treatment fluids comprising a reaction product of the present disclosure may be introduced to a subterranean formation in emulsified form and undergo a subsequent break (de-emulsification) therein to promote a desired action within the subterranean formation. In still other embodiments, the treatment fluids may promote de-emulsification of a fluid downhole, such as an emulsified hydrocarbon resource.

As used herein, the term "fracturing operation" refers to a high pressure operation that creates or extends a plurality of flow channels within a subterranean formation. As used herein, the term "fracturing fluid" refers to a viscosified fluid used in conjunction with a fracturing operation. A plurality of proppant particulates may be present in a fracturing fluid to maintain the flow channels created or extended in the fracturing operation in an open state.

As used herein, the term "remediation operation" refers to any operation designed to maintain, increase, or restore a specific rate of production from a wellbore, which may include stimulation operations or clean-up operations. As used herein, the term "remediation fluid" refers to any fluid used in conjunction with a remediation operation.

As used herein, the term "acidizing operation" refers to any operation designed to remove an acid-soluble material from a wellbore, such as an acid-soluble material that comprises at least a portion of the subterranean formation. As used herein, the term "acidizing fluid" refers to a fluid used during an acidizing operation. Mineral acids, such as hydrochloric acid or hydrobromic acid, or organic acids may be present in compositions utilized for acidizing a carbonate formation, whereas hydrofluoric acid may be present in compositions utilized for acidizing a siliceous formation.

As used herein, the term "spotting fluid" refers to a fluid designed for localized treatment of a subterranean formation. In one example, a spotting fluid can include a lost circulation material for treatment of a specific section of the wellbore, such as to seal off fractures in the wellbore and prevent sag. In another example, a spotting fluid can include a water control material or material designed to free a stuck piece of drilling or extraction equipment.

As used herein, the term "completion fluid" refers to a fluid used during the completion phase of a wellbore, including cementing compositions and cementing fluids.

As used herein, the term "cementing fluid" refers to a fluid used during cementing operations within a wellbore of a well.

Reaction products of the present disclosure may also be used in conjunction with enhanced oil recovery (EOR) operations. When used in conjunction with EOR operations, the reaction products of the present disclosure may change surface wetting within a subterranean formation to promote recovery of a hydrocarbon resource therefrom.

In any of the foregoing treatment operations, the treatment fluid may be foamed. Foamed fracturing fluids, for example, may be advantageous compared to viscosified treatment fluids for delivery of proppant particulates to a location in a wellbore. When foamed, treatment fluids may have a foam quality ranging from about 1% to about 99%.

Reaction products of the present disclosure may be present in any of the treatment fluids discussed above. Treatment fluids of the present disclosure may feature a concentration of the reaction product of about 0.1 gallons per thousand gallons (gpt) to about 10 gpt, or about 0.1 gpt to about 1 gpt, or about 0.2 gpt to about 0.5 gpt. These concentrations correspond to volume/volume percentages ranging from about 0.01% to about 1%, or from about 0.01% to about 0.1%, or from 0.02% to about 0.05%. The chosen concentration may vary depending upon the particular requirements for a given treatment operation and/or the specific subterranean conditions that are encountered downhole. In some examples, the reaction product may be present in a concentration effective to lower a surface tension for a neutral surfactant and/or zwitterionic surfactant also present in the treatment fluid.

Treatment fluids containing the reaction products of the present disclosure may optionally further comprise any number of additives that may be used in the oilfield services industry. Illustrative additives that may be present in a treatment fluid in combination with the reaction products of the present disclosure include, for example, surfactants, viscosifiers, gelling agents, gel stabilizers, anti-oxidants, polymer degradation prevention additives, relative permeability modifiers, scale inhibitors, corrosion inhibitors, chelating agents, foaming agents, defoaming agents, anti-foaming agents, emulsifying agents, de-emulsifying agents, iron control agents, proppants or other particulates, particulate diverters, salts, acids, fluid loss control additives, gas, catalysts, other clay control agents, dispersants, flocculants, scavengers (e.g., $H_2S$ scavengers, $CO_2$ scavengers or $O_2$ scavengers), lubricants, breakers, friction reducers, bridging agents, weighting agents, solubilizers, pH control agents (e.g., buffers), hydrate inhibitors, consolidating agents, bactericides, catalysts, the like, and any combination thereof. Suitable examples of these additives will be familiar to one having ordinary skill in the art.

Other Products

The compositions of the present disclosure comprising a reaction product of a dextrin compound, a dextran, or any combination thereof with a fatty acid obtained from a fatty ester may be formulated in a wide range of industrial or consumer products in which surfactants may be used. Personal care products may represent a beneficial class of products in which the compositions of the present disclosure may be present, given the relative benign nature of the biomolecules present in the compositions disclosed herein. Illustrative industrial and consumer products in which the compositions may be present are provided further below.

Adjuvants are compositions that are used in combination with an active substance to increase the efficacy or potency of the active substance. In non-limiting examples, the active substance may be a pharmaceutical compound, a personal care compound, or an agricultural compound.

The compositions of the present disclosure (e.g., a reaction product of a dextrin compound or a dextran and a fatty acid, as specified above, in combination with a neutral surfactant or a zwitterionic surfactant) may be present in adjuvant compositions in which surfactants of various types may be used. The compositions of the disclosure herein may replace a surfactant used in an adjuvant composition or be used in combination with a surfactant already present in an adjuvant composition. Within an adjuvant composition, the compositions may be present in an amount of about 0.01 wt. % to about 20 wt. % of the adjuvant composition as a whole, or about 0.1 wt. % to about 10 wt. %, or about 1 wt. % to about 15 wt. %, or about 5 wt. % to about 20 wt. %.

An active compound may be present in the adjuvant compositions, or an adjuvant composition may be administered separately from an active compound. When administered separately, the adjuvant compositions may be administered before or after the active compound.

Examples of suitable additional components that may be present in adjuvant compositions containing a reaction product of the present disclosure include, but are not limited to, other surfactants, anti-foam compounds, particulates, metal oxides (e.g., silica, alumina, titania, zirconia, and the like), electrolytes, salts, organic solvents, wetting agents, dispersants, emulsifying agents, de-emulsifying agents, penetrants, preservatives, colorants, acids, bases, buffers, chelating agents, viscosifiers, thixotropic agents, stabilizers, film-forming agents, plasticizers, preservatives, antioxidants, and the like, including any combination thereof. Other surfactants that may be present in the adjuvant compositions are not particularly limited and may include any one or a combination of cationic, anionic, neutral or zwitterionic surfactants.

Foaming agents are compositions that are a stabilized dispersion of a large volume of gas in the form of bubbles of varying sizes in a relatively small volume of liquid, or compositions that may form a foam upon suitable introduction of gas thereto (foamable formulations).

The compositions of the present disclosure (e.g., a reaction product of a dextrin compound or a dextran and a fatty acid, as specified above, in combination with a neutral surfactant or a zwitterionic surfactant, including the combination of a neutral surfactant and a zwitterionic surfactant in the case of forming a foam) may be present in foaming agents in which surfactants of various types may be used. The compositions of the disclosure herein may replace a surfactant used in a foaming agent or be used in combination with a surfactant already present in a foaming agent. Within a foaming agent, the compositions may be present in an amount of about 0.01 wt. % to about 20 wt. % of the foaming agent as a whole, or about 0.1 wt. % to about 10 wt. %, or about 1 wt. % to about 15 wt. %, or about 5 wt. % to about 20 wt. %.

Foaming agents may contain any combination of cationic surfactants, anionic surfactants, zwitterionic surfactants, or neutral surfactants. The compositions disclosed herein may be present in a foaming agent in combination with any of cationic surfactants, anionic surfactants, zwitterionic surfactants, neutral surfactants or any two or more of these surfactants. Alternately, the compositions disclosed herein may replace all or a portion of any one or more of these surfactants in a foaming agent. For example, the compositions of the present disclosure may replace anionic surfactants used in combination with zwitterionic surfactants in a foaming agent. That is, the compositions may be present in a foaming agent in combination with one or more zwitterionic surfactants. The compositions may replace a sulfosuccinate surfactant or be used in combination with a sulfosuccinate surfactant in some foaming agent embodiments, for example.

Examples of suitable additional components that may be present in foaming agents containing a reaction product of the present disclosure include, but are not limited to, other surfactants, amines (any one or a combination of primary amines, secondary amines, tertiary amines, diethanolamine, triethanolamine, ethoxylated amines and amidoamines), foam boosters such as amine oxides, solvents, water, salts, skin conditioners (e.g., ethylhexylglycerin, hydroxyethylurea, urea, panthenol, glycerin, isopropyl myristate, propylene glycol, tocopheryl acetate, and polyquaternium-11), moisturizers, liquefied gases, supercritical gases, acids, bases, salts, buffers, chelating agents, and the like, including any combination thereof. Suitable examples of these additional components will be familiar to one having ordinary skill in the art. Other surfactants that may be present in the foaming agents are not particularly limited and may include any one or a combination of cationic, anionic, neutral or zwitterionic surfactants.

Hard surface cleaners are compositions that may be used to remove various substances from surfaces like glass, metals, plastics, stone, concrete, and the like. Hard surfaces that may be cleaned with hard surface cleaners include, for example, windows, countertops, appliances, floors, driveways, toilets, showers and bathtubs, sinks, and the like. Substances removable from these types of hard surfaces and others span a wide range and include, but are not limited to, dirt, grease, soap scum, limescale and similar hard water deposits, and the like.

The compositions of the present disclosure (e.g., a reaction product of a dextrin compound or a dextran and a fatty acid, as specified above, in combination with a neutral surfactant or a zwitterionic surfactant) may be present in hard surface cleaners in which surfactants of various types may be used. The compositions of the disclosure herein may replace a surfactant used in a hard surface cleaner or be used in combination with a surfactant already present in a hard surface cleaner. Within a hard surface cleaner, the compositions may be present in an amount of about 0.01 wt. % to about 20 wt. % of the hard surface cleaner as a whole, or about 0.1 wt. % to about 10 wt. %, or about 1 wt. % to about 15 wt. %, or about 5 wt. % to about 20 wt. %.

Examples of suitable additional components that may be present in hard surface cleaners containing a reaction product of the present disclosure include, but are not limited to, other surfactants, foaming compounds, anti-foam compounds, salts such as alkali metal carbonates, organic solvents such as glycols or glycol ethers, wetting agents, dispersants, emulsifying agents, de-emulsifying agents, colorants, acids, bases, buffers, chelating agents, anti-streaking agents, alkanolamines, and the like, including any combination thereof Other surfactants that may be present in the hard surface cleaners are not particularly limited and may be any one or a combination of cationic, anionic, neutral or zwitterionic surfactants.

Skin creams and lotions are compositions that may moisturize or otherwise improve the appearance of skin. Skin creams and lotions are inclusive of gels formulation for application to the skin, which may have a higher viscosity than creams or lotions.

The compositions of the present disclosure (e.g., a reaction product of a dextrin compound or a dextran and a fatty ester, as specified above, in combination with a neutral surfactant or a zwitterionic surfactant) may be present in skin creams and lotions in which surfactants may be used. The compositions may replace a surfactant used in a skin cream or lotion or be used in combination with a surfactant already present in a skin cream or lotion. Within a skin cream or lotion, the compositions may be present in an amount of about 0.01 wt. % to about 20 wt. % of the skin cream or lotion as a whole, or about 0.1 wt. % to about 10 wt. %, or about 1 wt. % to about 15 wt. %, or about 5 wt. % to about 20 wt. %.

Examples of suitable additional components that may be present in skin creams or lotions disclosed herein include, but are not limited to, other surfactants, emulsifiers, essential oils, waxes, fats, solvents, viscosifying agents, mono-alcohols, diols, polyols, diol and polyol ethers, milk proteins, emollients, humectants, skin conditioners, preservatives, acids, bases, buffers, chelating agents, thickeners, vitamins, lubricants, wrinkle reducers, moisturizers, radical inhibitors and other antioxidants, Vitamin A, Vitamin E, ceramides, fatty acids, fatty esters, fatty alcohols, hyaluronic acid, sodium pyroglutamic acid, glycerin, aloe vera, fragrances, colorants, preservatives, sunscreens, and the like, including any combination thereof. Other surfactants that may be present in the skin creams and lotions are not particularly limited and may be any one or a combination of cationic, anionic, neutral or zwitterionic surfactants. The reaction products may replace at least a portion of one or more existing surfactants in a skin cream or lotion or supplement a quantity of one or more existing surfactants in a skin cream or lotion.

Body washes and shampoos are cleansing compositions formulated for application to the skin or hair. Liquid soaps for more generalized personal cleansing are similar in composition to some body washes and shampoos and may be formulated with many of the same components.

The compositions of the present disclosure (e.g., a reaction product of a dextrin compound or a dextran and a fatty acid, as specified above, in combination with a neutral surfactant or a zwitterionic surfactant) may be present in body washes, shampoos and liquid soaps in which surfactants may be used. The compositions of the disclosure herein may replace a surfactant used in a body wash, shampoo, or liquid soap or be used in combination with a surfactant already present in a body wash, shampoo or liquid soap. Within a body wash, shampoo, or liquid soap, the compositions may be present in an amount of about 0.01 wt. % to about 20 wt. % of the body wash, shampoo, or liquid soap as a whole, or about 0.1 wt. % to about 10 wt. %, or about 1 wt. % to about 15 wt. %, or about 5 wt. % to about 20 wt. %.

Examples of suitable additional components that may be present in body washes, shampoos, or liquid soaps disclosed herein include, but are not limited to, other surfactants, conditioners, amidoamines, fragrances, colorants, essential oils, foaming agents, humectants, fatty acids, fatty esters, fatty alcohols, waxes, biocides, soaps, preservatives, acids, bases, buffers, chelating agents, thickeners, vitamins, pearlizing agents, viscosifying agents, moisturizers, antioxidants, sunscreens, and the like, including any combination thereof. Illustrative examples of body washes, shampoos, and liquid soaps may comprise water, an effective amount of the compositions, optionally in further combination with another surfactant, 0-4% pearlizing agent, 0-1% suspension aids, 0-2% fragrance, 0-0.25% chelating agent, 0-1% preservatives, 0-2% colorant and 0-25% conditioner. Other surfactants that may be present in the body washes, shampoos, and liquid soaps are not particularly limited and may be any one or a combination of cationic, anionic, neutral or zwitterionic surfactants.

Sunscreens are substances that may be applied to the skin to afford protection from the sun. Sunscreens may be formulated as creams or with a suitable wax base in "stick" format for application to the skin.

The compositions of the present disclosure (e.g., a reaction product of a dextrin or dextran and a fatty ester, as specified above, in combination with a neutral surfactant or a zwitterionic surfactant) may be present in sunscreens in which surfactants may be used. The compositions of the disclosure herein may replace a surfactant used in a sunscreen or be used in combination with a surfactant already present in a sunscreen. Within a sunscreen, the compositions may be present in an amount of about 0.01 wt. % to about 20 wt. % of the sunscreen as a whole, or about 0.1 wt. % to about 10 wt. %, or about 1 wt. % to about 15 wt. %, or about 5 wt. % to about 20 wt. %.

Examples of suitable additional components that may be present in sunscreens include, but are not limited to, other surfactants, conditioners, titanium dioxide, zinc oxide, organic UV absorbers, film forming agents, solvents, aerosol propellants, waxes, fats, oils, moisturizers, fragrances, colorants, essential oils, fatty acids, fatty esters, fatty alcohols, preservatives, acids, bases, buffers, chelating agents, thickeners, insect repellents, skin conditioners, and the like, including any combination thereof. Other surfactants that may be present in the sunscreens are not particularly limited and may be any one or a combination of cationic, anionic, neutral or zwitterionic surfactants.

Organic UV absorbers that may be present in a sunscreen in combination with the compositions include, but are not limited to, para-aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, diethanolamine methoxycinnamate, digalloy trioleate, ethyl dihydroxypropyl PABA, glyceryl aminobenzoate, lawsone with dihydroxyacetone, red petrolatum, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, isopentyl 4-methoxycinnamate, phenylbenzimidazole sulfonate, 2-hydroxy-4-methoxy benzophenone-5-sulfonate, 4-(2-beta-glucopyrano-siloxy)propoxy-2-hydroxybenzophenone, and bis-sodium phenylene-1,4-bis(2-benzimidazyl)-3,3'-5,5'-tetrasulfonate, 2-ethylhexyl-p-methoxycinnamate, 4-tert-4'-methoxydibenzoylmethane, octocrylene, 2,4-bis-[{4-(2-ethythexyloxy)-2-hydroxy}-phenyl]-6-(4-methoxyphenyl)-1,3,5-triazine, methylene bis-benzotriazolyl tetrarnethyl butylphenol, 2,4,6-tris-[4-(2-ethylhexyloxycarbonyl)anilino]-1,3,5-triazine, diethylamino hydroxybenzoyl hexyl benzoate, oxybenzone, and dihydroxy dimethoxy benzophenone, and mixtures thereof.

Still other organic UV absorbers that may be suitable for inclusion in a sunscreen include, but are not limited to, bis-resorcinyl triazines; benzimidazole derivatives; 4-methylbenzylidene camphor; benzoyl piperazine derivatives; benzoxazole derivatives; diarylbutadiene derivatives; phenyl benzotriazole derivatives; benzylidene malonates; TEA-salicylate; imidazoline derivatives; naphthalates; merocyanine derivatives; aminobenzophenone derivatives; dibenzoylmethane derivatives; 3,3-diphenylacrylate derivatives; camphor derivatives; salicylate derivatives; anthranilate derivatives; and benzalmalonate derivatives.

In addition to formulations that are sunscreens alone, the compositions of the present disclosure may be present in sunscreens that are incorporated into other products such as lotions, cologne, cosmetics, body washes and shampoos, and the like.

Hair gels and hair sprays are formulations that may be used for holding one's hair in place, or optionally to provide detangling of one's hair. Hair sprays are aerosolized formations, whereas gels are high-viscosity fluids and may be applied by hand.

The compositions of the present disclosure (e.g., a reaction product of a dextrin or dextran and a fatty ester, as specified above, in combination with a neutral surfactant or a zwitterionic surfactant) may be present in hair sprays and hair gels in which surfactants may be used. The compositions of the disclosure herein may replace a surfactant used in a hair spray or hair gel or be used in combination with a surfactant already present in a hair spray or hair gel. Within a hair spray or hair gel, the compositions may be present in an amount of about 0.01 wt. % to about 20 wt. % of the hair gel or hair spray as a whole, or about 0.1 wt. % to about 10 wt. %, or about 1 wt. % to about 15 wt. %, or about 5 wt. % to about 20 wt. %.

Examples of suitable additional components that may be present in hair sprays or hair gels include, but are not limited to, other surfactants, cellulose-based biopolymers, water-soluble polymers, polyalkylene glycols, polyalkylene glycol esters, conditioning agents, emollients, humectants, emulsifiers, opacifying agents, thickening agents, foam stabilizers, viscosity builders, sequestrates, antioxidants, antidandruff agents, suspending agents, proteins, fragrances, sunscreens, botanical extracts, essential oils, fatty acids, fatty esters, fatty alcohols, preservatives, acids, bases, buffers, chelating agents, thickeners, vitamins, waxes, oils, aerosol propellants, polyvinylpyrrolidone, polyvinyl acetate, vinyl acetate-crotonic acid copolymers, acrylic acid copolymers, plasticizers, alcohols, and the like, including any combination thereof. Other surfactants that may be present in the hair sprays and hair gels are not particularly limited and may be any one or a combination of cationic, anionic, neutral or zwitterionic surfactants.

One or more examples of a hair spray or hair gel may comprise a composition of the present disclosure and one or more of cetearyl alcohol, behentrimonium chloride, cyclopentasiloxane, dimethicone, ethylhexyl isononanoate, behenyl alcohol, meadowfoam seed oil, cyclohexasiloxane, olive fruit oil, prunus amygdalus dulcis, stearamidopropyl dimethylamine, behentrimonium methosulfate, amodimethicone, panthenol, glycol stearate, ceteth-2, hydroxyethylcellulose, phenoxyethanol, methylparaben, propylparaben, citric acid, mica, titanium dioxide, iron oxide, fragrance, or any combination thereof.

One or more examples of a hair spray or hair gel may comprise a composition of the present disclosure and one or more of cyclomethicone, jojoba ester, dimethicone copolyol, nonfat dry milk, soy protein, stearic acid, capric/caprylic stearic triglyceride, jojoba oil, hybrid sunflower oil, cetearyl alcohol, glyceryl stearate, PEG-40 stearate, aloe vera gel, acrylates/$C_{10-30}$ alkyl acrylate crosspolymer, propylene glycol, tocopheryl acetate, methylparaben, propylparaben, fragrance, or any combination thereof.

Cosmetics are formulations that may be used for altering or improving one's physical appearance. Illustrative cosmetics include, but are not limited to, lipstick, blush, mascara, foundation, eyeliner, and the like. Forms of cosmetics may include, for example, emulsions, creams, gels, dispersions, sticks, and the like. Suitable emulsions within cosmetics may include oil-in-water or water-in-oil emulsions.

The compositions of the present disclosure (e.g., a reaction product of a dextrin or dextran and a fatty ester, as specified above, in combination with a neutral surfactant or a zwitterionic surfactant) may be present in various types of cosmetics in which surfactants may be used. The compositions of the disclosure herein may replace a surfactant used in a cosmetic or be used in combination with a surfactant already present in a cosmetic. Within a cosmetic, the compositions may be present in an amount of about 0.01 wt. % to about 20 wt. % of the cosmetic as a whole, or about 0.1 wt. % to about 10 wt. %, or about 1 wt. % to about 15 wt. %, or about 5 wt. % to about 20 wt. %.

Examples of suitable additional components that may be present in cosmetics include, but are not limited to, other surfactants, perfumes, preservatives, coloring materials, UV absorbers, moisture-retaining agents, emulsifiers, gelling agents, oils, thickening agents, foam stabilizers, viscosity builders, preservatives, sequestrates, antioxidants, suspending agents, proteins, fragrances, sunscreens, botanical extracts, essential oils, fats (e.g., shea butter, mango seed butter, and cacao seed butter), fatty acids, fatty esters, fatty alcohols, biocides, soaps, preservatives, acids, bases, buffers, chelating agents, thickeners, vitamins, waxes (e.g., myristyl myristate, *Camellia sinensis* leaf extract, jojoba, sunflower seed, carnauba wax, candelilla wax, and beeswax), and the like, including any combination thereof. Some examples of components that may be present in cosmetics may include, for example, higher fatty alcohols such as cetyl alcohol, stearyl alcohol and behenyl alcohol; higher fatty acid including caprylic/capric triglyceride, lauric acid, myristic acid, palmitic acid and stearic acid; hydrocarbons including ceresin; natural oils including meadowfoam seed oil, sunflower seed oil, macadamia seed oil, green tea seed oil, ginger oil, ginseng oil, coconut oil, olive oil and camellia oil; esters including phytosteryl/octyldodecyl lauroyl glutamate, isostearyl isostearate, methylheptyl isostearate, dicaprylyl carbonate and isopropyl palmitate; ethers including dicaprylyl ether; silicone oils including dimethicone, cyclopentasiloxane, cyclohexasiloxane, phenyltrimethicone, trisiloxane and methyltrimethicone; and hydrocarbons including squalane. Other surfactants that may be present in the cosmetics are not particularly limited and may be any one or a combination of cationic, anionic, neutral or zwitterionic surfactants. Cosmetics of the present disclosure may be formulated in any suitable form including, sticks, creams, powders, gels, and the like.

Deodorants and antiperspirants are formulations that may be utilized for controlling body odor. Deodorants and antiperspirants of the present disclosure may be formulated in stick form, gel form, powder form or aerosolizable form.

The compositions of the present disclosure (e.g., a reaction product of a dextrin or dextran and a fatty ester, as specified above, in combination with a neutral surfactant or a zwitterionic surfactant) may be present in deodorants and antiperspirants in which surfactants may be used. The compositions of the disclosure herein may replace a surfactant used in a deodorant or antiperspirant or be used in combination with a surfactant already present in a deodorant or antiperspirant. Within a deodorant or antiperspirant, the compositions may be present in an amount of about 0.01 wt. % to about 20 wt. % of the deodorant or antiperspirant as a whole, or about 0.1 wt. % to about 10 wt. %, or about 1 wt. % to about 15 wt. %, or about 5 wt. % to about 20 wt. %.

Examples of suitable additional components that may be present in deodorants or antiperspirants disclosed herein include, but are not limited to, other surfactants, aluminum salts (e.g., alum, aluminum chloride, aluminum chlorohydrate, aluminum-zirconium compounds, aluminum-zirconium tetrachlorohydrex gly, and aluminum-zirconium tetrachlorohydrex gly), anti-bacterial agents, parabens, alcohols, propylene glycol, hexamethylenetetramine, acids, bases, buffers, chelating agents, perfumes, preservatives, coloring materials, moisture-absorbing agents (desiccants), emulsifiers, gelling agents, oils, thickening agents, foam stabilizers, viscosity builders, sequestrates, antioxidants, suspending agents, fragrances, essential oils, fats, fatty acids, fatty esters, fatty alcohols, waxes, and the like, including any combination thereof. Other surfactants that may be present in the deodorants and antiperspirants are not particularly limited and may be any one or a combination of cationic, anionic, neutral or zwitterionic surfactants. Deodorants and antiperspirants of the present disclosure may be formulated in any suitable form including, sticks, creams, powders, gels, and the like.

The compositions of the present disclosure comprising a reaction product of a dextrin compound, a dextran, or any combination thereof with a fatty ester may also find exemplary uses and formulations outside the personal care space as well. In addition to the oilfield applications described above, the compositions of the present disclosure may be incorporated in applications in which metal sequestration from a fluid is needed, such as within froth floatation processes. Froth floatation processes may be conducted in various instances, such as mining runoff or wastewater treatment. In such applications, the compositions of the present disclosure may replace a surfactant used in froth floatation or be used in combination with a surfactant already present in froth floatation process. Within a given froth floatation process, the compositions may be present in an amount of about 0.01 wt. % to about 20 wt. % of a froth floatation fluid as a whole, or about 0.1 wt. % to about 10 wt. %, or about 1 wt. % to about 15 wt. %, or about 5 wt. % to about 20 wt. %.

In some examples, the compositions of the present disclosure may be utilized in roughers and cleaner circuits to promote clay dispersion, water conditioning, additive enhancement and/or emulsification of metal suppressants such as Mn and Fe. Any conventional frothing agent may be utilized in combination with the compositions disclosed herein. Suitable frothing agents and details concerning frothing agents will be familiar to one having ordinary skill in the art.

Embodiments disclosed herein include:

A. Compositions comprising a saccharide polymer reaction product with a fatty ester. The compositions comprise: an aqueous phase; a neutral surfactant or a reaction product form thereof; a reaction product of a saccharide polymer and a fatty ester, the saccharide polymer comprising a dextran, a dextrin compound, or any combination thereof, and the reaction product of the saccharide polymer and the fatty ester and the reaction product form of the neutral surfactant, if present, being formed in the aqueous phase in the presence of a hydroxide base; and one or more alcohols originating from the fatty ester upon forming the reaction product of the saccharide polymer and the fatty ester; wherein the reaction product of the saccharide polymer and the fatty ester is present in the aqueous phase at a concentration effective to lower a surface tension of the neutral surfactant.

A1. The composition of A, wherein the saccharide polymer comprises dextran.

A2. The composition of A, wherein the saccharide polymer comprises a dextrin compound.

B. Methods for functionalizing a polysaccharide. The methods comprise: heating a saccharide polymer, a fatty ester, a neutral surfactant, and a hydroxide base in an aqueous phase, the saccharide polymer comprising a dextran, a dextrin compound, or any combination thereof; and obtaining a reaction product of the saccharide polymer and the fatty ester in the aqueous phase, the aqueous phase also containing the neutral surfactant or a reaction product form thereof, and one or more alcohols originating from the fatty ester upon forming the reaction product of the saccharide polymer and the fatty ester.

B1. The method of B, wherein the saccharide polymer comprises dextran.

B2. The method of B, wherein the saccharide polymer comprises a dextrin compound.

A personal care product comprising the composition of A, A1 or A2.

Embodiments A, A1, A2, B, B1, and B2 may have one or more of the following element present in any combination.

Element 1: wherein the saccharide polymer comprises a dextrin compound, and the dextrin compound comprises a maltodextrin.

Element 2: wherein the maltodextrin has a dextrose equivalent value of about 3 to about 25, or wherein the maltodextrin has a dextrose equivalent value of about 4.5 to about 7.0, or wherein the maltodextrin has a dextrose equivalent value of about 9.0 to about 12.0.

Element 3: wherein the fatty ester comprises a glycerol ester.

Element 4: wherein the one or more alcohols comprise at least glycerol.

Element 5: wherein the glycerol ester comprises up to three types of fatty acids having about 4 to about 30 carbon atoms.

Element 6: wherein the glycerol ester comprises at least one plant oil, animal oil, vegetable fat, or animal fat selected from the group consisting of soybean oil, grapeseed oil, olive oil, palm oil, tea seed oil, rice bran oil, safflower oil, corn oil, coconut oil, sunflower seed oil, canola oil, rapeseed oil, peanut oil, cottonseed oil, hazelnut oil, linseed oil, sesame oil, acai oil, almond oil, beech nut oil, brazil nut oil, cashew oil, macadamia nut oil, pecan oil, pine nut oil, pistachio oil, walnut oil, pumpkin seed oil, apricot oil, avocado oil, grapefruit oil, lemon oil, orange oil, mango oil, flax seed oil, fish oil, cocoa butter, hemp oil, castor oil, tall oil, fish oil, cattle fat, buffalo fat, sheep fat, goat fat, duck fat, pig fat, poultry fat, and any combination thereof.

Element 7: wherein the aqueous phase comprises about 7.5 wt. % to about 20 wt. % glycerol relative to fatty acids originating from the glycerol ester.

Element 8: wherein the neutral surfactant comprises an alkanolamide or a reaction product thereof.

Element 9: wherein the alkanolamide comprises a compound selected from the group consisting of cocamide diethanolamine, cocamide monoethanolamine, cocamide diisopropanolamine, and any combination thereof.

Element 10: wherein a molar ratio of fatty acid to saccharide polymer in the reaction product is about 0.2 or above on a basis of $moles_{fatty\ acid\ in\ fatty\ ester}$:$moles_{glucose\ monomers\ in\ saccharide\ polymer}$.

Element 11: wherein the reaction product of the saccharide polymer comprises a fatty ester saccharide reaction product.

Element 12: wherein the reaction product of the saccharide polymer and the fatty ester is present in the aqueous phase at a concentration effective to lower a surface tension of the neutral surfactant.

By way of non-limiting example, exemplary combinations applicable to A, A1, A2, B, B1, and B2 include, but are not limited, to: 1 and 2; 1 and 3; 1 and 4; 1, 3 and 4; 1, 3 and 5; 1 and 7; 1, 3, 5 and 7; 1 and 8; 1, 8 and 9; 1 and 11; 2 and 3; 2 and 4; 2, 3 and 4; 2, 3 and 5; 1 and 7; 2, 3, 5, and 7; 2 and 8; 2, 8 and 9; 3 and 4; 3 and 5; 3 and 7; 3, 5, and 7; 3 and 8; 3, 8 and 9; 8 and 8; 7, 8 and 9; and 8 and 9.

Additional embodiments disclosed herein are directed to the following non-limiting clauses:

Clause 1. A composition comprising:
- an aqueous phase;
- a neutral surfactant or a reaction product form thereof;
- a reaction product of a saccharide polymer and a fatty ester, the saccharide polymer comprising a dextran, a dextrin compound, or any combination thereof, and the reaction product of the saccharide polymer and the fatty ester and the reaction product form of the neutral surfactant, if present, being formed in the aqueous phase in the presence of a hydroxide base; and
- one or more alcohols originating from the fatty ester upon forming the reaction product of the saccharide polymer and the fatty ester;
  - wherein the reaction product of the saccharide polymer and the fatty ester is present in the aqueous phase at a concentration effective to lower a surface tension of the neutral surfactant.

Clause 2. The composition of clause 1, wherein the saccharide polymer comprises a dextrin compound, and the dextrin compound comprises a maltodextrin.

Clause 3. The composition of clause 1, wherein the fatty ester comprises a glycerol ester of at least one fatty acid, and the one or more alcohols comprise at least glycerol.

Clause 4. The composition of clause 3, wherein the at least one fatty acid comprises up to three types of fatty acids having about 4 to about 30 carbon atoms.

Clause 5. The composition of clause 3, wherein the at least one fatty acid consists of straight-chain fatty acids.

Clause 6. The composition of clause 3, wherein at least a portion of the at least one fatty acid comprises one or more unsaturated straight-chain fatty acids.

Clause 7. The composition of clause 3, wherein the glycerol ester comprises at least one plant oil, animal oil, vegetable fat, or animal fat selected from the group consisting of soybean oil, grapeseed oil, olive oil, palm oil, tea seed oil, rice bran oil, safflower oil, corn oil, coconut oil, sunflower seed oil, canola oil, rapeseed oil, peanut oil, cottonseed oil, hazelnut oil, linseed oil, sesame oil, acai oil, almond oil, beech nut oil, brazil nut oil, cashew oil, macadamia nut oil, pecan oil, pine nut oil, pistachio oil, walnut oil, pumpkin seed oil, apricot oil, avocado oil, grapefruit oil, lemon oil, orange oil, mango oil, flax seed oil, fish oil, cocoa butter, hemp oil, castor oil, tall oil, fish oil, cattle fat, buffalo fat, sheep fat, goat fat, duck fat, pig fat, poultry fat, and any combination thereof.

Clause 8. The composition of clause 3, wherein the aqueous phase comprises about 7.5 wt. % to about 20 wt. % glycerol relative to the one or more fatty acids originating from the glycerol ester.

Clause 9. The composition of clause 1, wherein the fatty ester is formed from at least one fatty acid, and the at least one fatty acid comprises about 90 wt. % or above of one or more straight-chain fatty acids.

Clause 10. The composition of clause 1, wherein the neutral surfactant comprises an alkanolamide or a reaction product thereof.

Clause 11. The composition of clause 11, wherein the alkanolamide comprises a compound selected from the group consisting of cocamide diethanolamine, cocamide monoethanolamine, cocamide diisopropanolamine, and any combination thereof.

Clause 12. The composition of clause 1, wherein a molar ratio of fatty acid to saccharide polymer in the reaction product is about 0.2 or above on a basis of $\mathrm{moles}_{fatty\ acid\ in\ fatty\ ester} : \mathrm{moles}_{glucose\ monomers\ in\ saccharide\ polymer}$.

Clause 13. The composition of clause 1, wherein a molar ratio of fatty acid to saccharide polymer in the reaction product is about 0.2 to about 0.9 on a basis of $\mathrm{moles}_{fatty\ acid\ in\ fatty\ ester} : \mathrm{moles}_{glucose\ monomers\ in\ saccharide\ polymer}$.

Clause 14. The composition of clause 1, wherein the reaction product of the saccharide polymer comprises a fatty ester saccharide polymer reaction product.

Clause 15. A personal care product comprising the composition of clause 1.

Clause 16. A method comprising: heating a saccharide polymer, a fatty ester, a neutral surfactant, and a hydroxide base in an aqueous phase, the saccharide polymer comprising a dextran, a dextrin compound, or any combination thereof; and obtaining a reaction product of the saccharide polymer and the fatty ester in the aqueous phase, the aqueous phase also containing the neutral surfactant or a reaction product form thereof, and one or more alcohols originating from the fatty ester upon forming the reaction product of the saccharide polymer and the fatty ester.

Clause 17. The method of clause 16, wherein the saccharide polymer comprises a dextrin compound, and the dextrin compound comprises a maltodextrin.

Clause 18. The method of clause 16, wherein the fatty ester comprises a glycerol ester of at least one fatty acid, and the one or more alcohols comprise at least glycerol.

Clause 19. The method of clause 18, wherein the at least one fatty acid comprises up to three types of fatty acids having about 4 to about 30 carbon atoms.

Clause 20. The method of clause 18, wherein the at least one fatty acid consists of straight-chain fatty acids.

Clause 21. The method of clause 18, wherein at least a portion of the at least one fatty acid comprises one or more unsaturated straight-chain fatty acids.

Clause 22. The method of clause 18, wherein the glycerol ester comprises at least one plant oil, animal oil, vegetable fat, or animal fat selected from the group consisting of soybean oil, grapeseed oil, olive oil, palm oil, tea seed oil, rice bran oil, safflower oil, corn oil, coconut oil, sunflower seed oil, canola oil, rapeseed oil, peanut oil, cottonseed oil, hazelnut oil, linseed oil, sesame oil, acai oil, almond oil, beech nut oil, brazil nut oil, cashew oil, macadamia nut oil, pecan oil, pine nut oil, pistachio oil, walnut oil, pumpkin seed oil, apricot oil, avocado oil, grapefruit oil, lemon oil, orange oil, mango oil, flax seed oil, fish oil, cocoa butter, hemp oil, castor oil, tall oil, fish oil, cattle fat, buffalo fat, sheep fat, goat fat, duck fat, pig fat, poultry fat, and any combination thereof.

Clause 23. The method of clause 18, wherein the aqueous phase comprises about 7.5 wt. % to about 20 wt. % glycerol relative to the one or more fatty acids originating from the glycerol ester.

Clause 24. The method of clause 16, wherein the fatty ester is formed from at least one fatty acid, and the at least one fatty acid comprises about 90 wt. % or above of one or more straight-chain fatty acids.

Clause 25. The method of clause 16, wherein the neutral surfactant comprises an alkanolamide or a reaction product thereof.

Clause 26. The method of clause 25, wherein the alkanolamide comprises a compound selected from the group consisting of cocamide diethanolamine, cocamide monoethanolamine, cocamide diisopropanolamine, and any combination thereof.

Clause 27. The method of clause 16, wherein a molar ratio of fatty acid to saccharide polymer in the reaction product is about 0.2 or above on a basis of $moles_{fatty\ acid\ in\ fatty\ ester} : moles_{glucose\ monomers\ in\ saccharide\ polymer}$.

Clause 28. The method of clause 16, wherein a molar ratio of fatty acid to saccharide polymer in the reaction product is about 0.2 to about 0.9 on a basis of $moles_{fatty\ acid\ in\ fatty\ ester} : moles_{glucose\ monomers\ in\ saccharide\ polymer}$.

Clause 29. The method of clause 16, wherein the reaction product of the saccharide polymer comprises a fatty ester saccharide polymer reaction product.

Clause 30. The method of clause 16, wherein the reaction product of the saccharide polymer and the fatty ester is present in the aqueous phase at a concentration effective to lower a surface tension of the neutral surfactant.

To facilitate a better understanding of the disclosure herein, the following examples of various representative embodiments are given. In no way should the following examples be read to limit, or to define, the scope of the invention.

EXAMPLES

Example 1 (Experimental): General Procedure for Preparation of Maltodextrin Reactions Products Using a Glycerol Ester 25.00 g cocamide diethanolamine (CocoDEA) and 10.00 g KOH (45% active solution) were combined in water. The reaction mixture was mechanically stirred and heated to 65° C. Thereafter, soybean oil and 150.0 g maltodextrin (MALTRIN M100, Grain Processing Corporation, Muscatine, Iowa; DE=9.0–12.0) as a 30% active solution were added to the reaction mixture. The amount of soybean oil was selected to provide a HLB of either 12 or 16 upon formation of a reaction product. The amount of water was selected to provide a surfactant concentration of 5 wt. %, a fatty ester (oil) concentration of 2.5 wt. %, and a maltodextrin concentration of 10 wt. %, based on all reaction components. Once the maltodextrin dissolved, heating was discontinued and stirring was conducted until the reaction mixture reached room temperature. The resulting aqueous phase containing the reaction products was used without further processing for the additional testing below. Dextran reaction products may be formed using a similar procedure.

Example 2 (Comparative): General Procedure for Preparation of Maltodextrin Reaction Products Using Free Fatty Acids 25.00 g cocamide diethanolamine (CocoDEA) and 10.00 g KOH (45% active solution) were combined in water. The reaction mixture was mechanically stirred and heated to 65° C. Thereafter, a fatty acid mixture containing saturated fatty acids and 150.0 g maltodextrin (MALTRIN M100, Grain Processing Corporation, Muscatine, Iowa; DE=9.0–12.0) as a 30% active solution were added to the reaction mixture. The amount of the fatty acid mixture was selected to provide a HLB of either 12 or 16. The amount of water was selected to provide a surfactant concentration of 5 wt. %, a fatty acid concentration of 2.5 wt. %, and a maltodextrin concentration of 10 wt. %, based on all reaction components. Once the maltodextrin dissolved, heating was discontinued and stirring was conducted until the reaction mixture reached room temperature. The resulting aqueous phase containing the reaction products was used without further processing for the additional testing below. Dextran reaction products may be formed using a similar procedure.

Surface Tension Measurements. Surface tension (ST) measurements were made using a Bolin Scientific Tensiometer at room temperature. The reaction products from Examples 1 and 2 were formulated at concentrations of 0.5 gpt (gallons per thousand gallons), 1 gpt and 2 gpt in deionized water. Surface tension results are summarized in Table 1 below.

TABLE 1

| Entry | Sample Description | Surface Tension (dynes/cm) | | |
|---|---|---|---|---|
| | | 2 gpt | 1 gpt | 0.5 gpt |
| 1A (exp) | Example 1, HLB = 16 | 27.5 | 27.7 | 30.0 |
| 1B (exp) | Example 1, HLB = 12 | 27.6 | 31.4 | 34.3 |
| 2A (comp) | Example 2, HLB = 16 | 28.2 | 30.6 | 35.4 |
| 2B (comp) | Example 2, HLB = 12 | 28.3 | 29.2 | 35.6 |
| 3A (exp) | Example 1 w/additional 10 wt. % glycerol (based on soybean oil) added before heating, HLB = 16 | 27.8 | 29.2 | 31.5 |
| 3B (exp) | Example 1 w/additional 10 wt. % glycerol (based on soybean oil) added before heating, HLB = 12 | 30.6 | 33.2 | 34.9 |
| 4A (exp) | Example 1 w/additional 10 wt. % glycerol (based on soybean oil) added after heating, HLB = 16 | 27.5 | 27.8 | 31.0 |
| 4B (exp) | Example 1 w/additional 10 wt. % glycerol (based on soybean oil) added after heating, HLB = 12 | 32.4 | 32.9 | 35.3 |
| 5A (comp) | Example 2 w/additional 10 wt. % glycerol (based on soybean oil) added before heating, HLB = 16 | 28.3 | 29.7 | 32.4 |
| 5B (comp) | Example 2 w/additional 10 wt. % glycerol (based on soybean oil) added before heating, HLB = 12 | 28.1 | 29.7 | 31.8 |
| 6A (comp) | Example 2 w/additional 10 wt. % glycerol (based on soybean oil) added after heating, HLB = 16 | 28.1 | 29.1 | 31.1 |
| 6B (comp) | Example 2 w/additional 10 wt. % glycerol (based on soybean oil) added after heating, HLB = 12 | 28.0 | 29.0 | 30.4 |
| 7 (control) | 5 wt. % CocoDEA in water (heated as in Example 1) | 31.9 | 34.5 | — |
| 8 (control) | 5 wt. % CocoDEA in 2% aqueous KOH (45% active solution) (heated as in Example 1) | 35.0 | 36.7 | — |

TABLE 1-continued

| Entry | Sample Description | Surface Tension (dynes/cm) | | |
|---|---|---|---|---|
| | | 2 gpt | 1 gpt | 0.5 gpt |
| 9 (control) | 2.5 wt. % soybean oil, 10 wt. % maltodextrin and 5 wt. % CocoDEA in water, heated as Example 1 | 30.0 | 33.0 | 41.4 |
| 10 (control) | 2.5 wt. % soybean oil, 10 wt. % maltodextrin and 5 wt. % CocoDEA in water, no heating | 29.9 | 34.9 | 42.8 |
| 11 (control) | 10 wt. % maltodextrin (30% active solution), 5 wt. % CocoDEA in water, heated as Example 1 | 35.9 | 49.2 | — |

As shown, both soybean oil (Entries 1A/1B) and mixed fatty acids (Entries 2A/2B) afforded a decrease in surface tension compared to CocoDEA alone (Entry 10). Surprisingly, soybean oil afforded slightly better surface tension performance than did mixed fatty acids in most instances. This result is particularly surprising in light of the fact that a combination of mixed fatty acids and glycerol (Entries 5A/5B and 6A/6B), gave surface tension values comparable to those produced with mixed fatty acids alone (Entries 2A/2B). That is, glycerol introduced to the reaction mixture to simulate the amount in wt. % released during soybean oil alkaline hydrolysis did not appreciably impact the surface tension performance, except at 0.5 gpt, in which case the added glycerol afforded slightly better surface tension performance. Introduction of additional glycerol over that released during alkaline hydrolysis of soybean oil (Entries 3A/3B and 4A/4B) resulted in slightly higher surface tension values. The lowering of the surface tension is further surprising in light of the tendency of the individual reaction components to raise surface tension values (comparing Entries 8-11 against Entry 7).

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, compositions, tools and methods are described herein in terms of "comprising" various components or steps, the systems, compositions, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, compositions, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, compositions, tools and methods illustratively disclosed herein may suitably be practiced in the absence of any element that is not specifically disclosed herein and/or any optional element disclosed herein. While systems, compositions, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A composition comprising:
   an aqueous phase;
   a neutral surfactant or a reaction product form thereof;
   a reaction product of a saccharide polymer and a fatty ester, the saccharide polymer comprising a dextran, a dextrin compound, or any combination thereof, and the reaction product of the saccharide polymer and the fatty ester and the reaction product form of the neutral surfactant, if present, being formed in the aqueous phase in the presence of a hydroxide base;

wherein the reaction product form of the neutral surfactant, if present, comprises a fatty ester reaction product formed from a hydroxyl group upon the neutral surfactant; and
one or more alcohols originating from the fatty ester upon forming the reaction product of the saccharide polymer and the fatty ester;
wherein the reaction product of the saccharide polymer and the fatty ester is present in the aqueous phase at a concentration effective to lower a surface tension of the neutral surfactant.

2. The composition of claim 1, wherein the saccharide polymer comprises a dextrin compound, and the dextrin compound comprises a maltodextrin.

3. The composition of claim 1, wherein the fatty ester comprises a glycerol ester of at least one fatty acid, and the one or more alcohols comprise at least glycerol.

4. The composition of claim 3, wherein the at least one fatty acid comprises up to three types of fatty acids having about 4 to about 30 carbon atoms.

5. The composition of claim 3, wherein the at least one fatty acid consists of straight-chain fatty acids.

6. The composition of claim 3, wherein at least a portion of the at least one fatty acid comprises one or more unsaturated straight-chain fatty acids.

7. The composition of claim 3, wherein the glycerol ester comprises at least one plant oil, animal oil, vegetable fat, or animal fat selected from the group consisting of soybean oil, grapeseed oil, olive oil, palm oil, tea seed oil, rice bran oil, safflower oil, corn oil, coconut oil, sunflower seed oil, canola oil, rapeseed oil, peanut oil, cottonseed oil, hazelnut oil, linseed oil, sesame oil, acai oil, almond oil, beech nut oil, brazil nut oil, cashew oil, macadamia nut oil, pecan oil, pine nut oil, pistachio oil, walnut oil, pumpkin seed oil, apricot oil, avocado oil, grapefruit oil, lemon oil, orange oil, mango oil, flax seed oil, fish oil, cocoa butter, hemp oil, castor oil, tall oil, fish oil, cattle fat, buffalo fat, sheep fat, goat fat, duck fat, pig fat, poultry fat, and any combination thereof.

8. The composition of claim 1, wherein the fatty ester is formed from at least one fatty acid, and the at least one fatty acid comprises about 90 wt. % or above of one or more straight-chain fatty acids.

9. The composition of claim 1, wherein the neutral surfactant comprises an alkanolamide or a reaction product thereof.

10. The composition of claim 1, wherein a molar ratio of fatty acid to saccharide polymer in the reaction product is about 0.2 to about 0.9 on a basis of $moles_{fatty\ acid\ in\ fatty\ ester} : moles_{glucose\ monomers\ in\ saccharide\ polymer}$.

11. A personal care product comprising the composition of claim 1.

12. A method comprising:
heating a saccharide polymer, a fatty ester, a neutral surfactant, and a hydroxide base in an aqueous phase, the saccharide polymer comprising a dextran, a dextrin compound, or any combination thereof; and
obtaining a reaction product of the saccharide polymer and the fatty ester in the aqueous phase, the aqueous phase also containing the neutral surfactant or a reaction product form thereof, and one or more alcohols originating from the fatty ester upon forming the reaction product of the saccharide polymer and the fatty ester;
wherein the reaction product form of the neutral surfactant, if present, comprises a fatty ester reaction product formed from a hydroxyl group upon the neutral surfactant.

13. The method of claim 12, wherein the saccharide polymer comprises a dextrin compound, and the dextrin compound comprises a maltodextrin.

14. The method of claim 12, wherein the fatty ester comprises a glycerol ester of at least one fatty acid, and the one or more alcohols comprise at least glycerol.

15. The method of claim 14, wherein the at least one fatty acid comprises up to three types of fatty acids having about 4 to about 30 carbon atoms.

16. The method of claim 14, wherein the at least one fatty acid consists of straight-chain fatty acids.

17. The method of claim 14, wherein at least a portion of the at least one fatty acid comprises one or more unsaturated straight-chain fatty acids.

18. The method of claim 14, wherein the glycerol ester comprises at least one plant oil, animal oil, vegetable fat, or animal fat selected from the group consisting of soybean oil, grapeseed oil, olive oil, palm oil, tea seed oil, rice bran oil, safflower oil, corn oil, coconut oil, sunflower seed oil, canola oil, rapeseed oil, peanut oil, cottonseed oil, hazelnut oil, linseed oil, sesame oil, acai oil, almond oil, beech nut oil, brazil nut oil, cashew oil, macadamia nut oil, pecan oil, pine nut oil, pistachio oil, walnut oil, pumpkin seed oil, apricot oil, avocado oil, grapefruit oil, lemon oil, orange oil, mango oil, flax seed oil, fish oil, cocoa butter, hemp oil, castor oil, tall oil, fish oil, cattle fat, buffalo fat, sheep fat, goat fat, duck fat, pig fat, poultry fat, and any combination thereof.

19. The method of claim 12, wherein the fatty ester is formed from at least one fatty acid, and the at least one fatty acid comprises about 90 wt. % or above of one or more straight-chain fatty acids.

20. The method of claim 12, wherein the neutral surfactant comprises an alkanolamide or a reaction product thereof.

21. The method of claim 12, wherein a molar ratio of fatty acid to saccharide polymer in the reaction product is about 0.2 to about 0.9 on a basis of $moles_{fatty\ acid\ in\ fatty\ ester} : moles_{glucose\ monomers\ in\ saccharide\ polymer}$.

* * * * *